US00PP14385P39

(12) United States Plant Patent
Murakami

(10) Patent No.: US PP14,385 P3
(45) Date of Patent: Dec. 16, 2003

(54) PETUNIA PLANT NAMED 'SUNBEL-APU'

(50) Latin Name: *Petunia hybrida*
Varietal Denomination: Sunbel-Apu

(75) Inventor: Yasuyuki Murakami, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 10/107,192

(22) Filed: Mar. 28, 2002

(65) Prior Publication Data

US 2003/0188366 P1 Oct. 2, 2003

(51) Int. Cl.[7] ..... A01H 5/00
(52) U.S. Cl. ..... Plt./356
(58) Field of Search ..... Plt./356

(56) References Cited

U.S. PATENT DOCUMENTS

| | | | |
|---|---|---|---|
| PP6,899 | P | 7/1989 | Tsuda et al. |
| PP6,914 | P | 7/1989 | Tsuda et al. |
| PP6,915 | P | 7/1989 | Tsuda et al. |
| PP8,489 | P | 12/1993 | Hirabayashi et al. |
| PP8,768 | P | 6/1994 | Hirabayashi et al. |
| PP9,322 | P | 10/1995 | Tachibana et al. |
| PP9,341 | P | 10/1995 | Tachibana et al. |
| PP9,342 | P | 10/1995 | Sakazaki et al. |
| PP9,556 | P | 5/1996 | Tachibana et al. |
| PP9,557 | P | 5/1996 | Suzuki et al. |
| PP9,754 | P | 12/1996 | Suzuki et al. |
| PP10,045 | P | 9/1997 | Rother |
| PP10,278 | P | 3/1998 | Murakami |
| PP10,279 | P | 3/1998 | Murakami |
| PP10,287 | P | 3/1998 | Murakami |
| PP10,310 | P | 3/1998 | Sakazaki |
| PP10,330 | P | 4/1998 | Sakazaki |
| PP10,355 | P | 4/1998 | Murakami |
| PP10,904 | P | 5/1999 | Hansson |
| PP11,006 | P | 7/1999 | Danziger |
| PP11,352 | P | 4/2000 | Murakami |
| PP11,558 | P | 10/2000 | Murakami |
| PP12,101 | P2 | 9/2001 | Sakazaki |

OTHER PUBLICATIONS

UPOV–ROM, Plant Variety Database, hit on 'Sunbel–apu', 2002/05.*

The Plant Book, A Portable Dictionary of the Vascular Plants, Second Edition, D.J. Mabberley, Cambridge University Press, Cover Pages and p. 115 (1997).

Official Gazette of Japan, two pages (Jun. 14, 2001).

Flower & Green 2001 Catalog, Cover page plus two pages (Sep. or Oct. 2000).

* cited by examiner

*Primary Examiner*—Anne Marie Grunberg
(74) *Attorney, Agent, or Firm*—Burns, Doane, Swecker & Mathis, L.L.P.

(57) ABSTRACT

A new and distinct variety of Petunia plant having a semi-erect habit is provided. The new Petunia plant has abundant branching particularly with respect to the secondary branching and a great profusion of blooms with the entire plant remaining in bloom for a considerable period of time. The flowers are very small with light yellowish pink petals that are formed in profusion in a spike. The blooming period commonly is from May to September. The plant exhibits high resistance to cold, rain, heat drought, and diseases, such as Powdery Mildew.

1 Drawing Sheet

Figure 1:
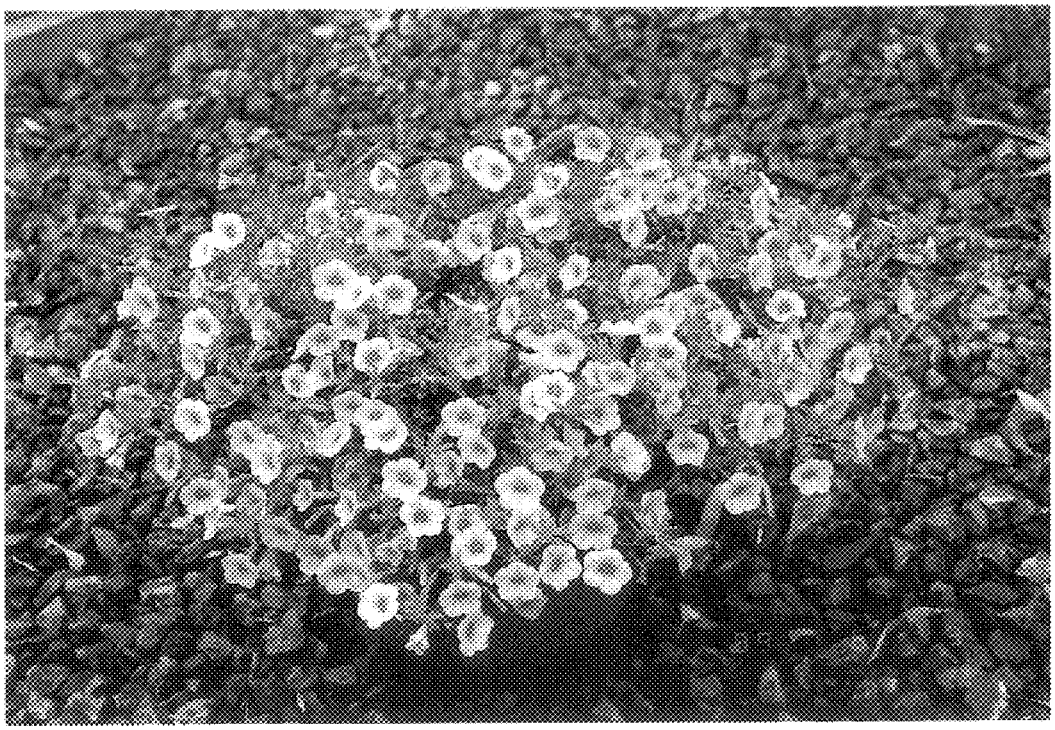

Botanical/commercial classification: *Petunia hybrida*/Petunia Plant.
Varietal denomination: cv. 'Sunbel-Apu'.

BACKGROUND OF THE VARIETY

The Petunia is a very popular plant and is used for flower bedding and potting in the summer season. There are only a few varieties of the Petunia plants that do not have an upright growth habit and which have a high resistance to rain, heat, cold and diseases. Recently, there were developed a series of small-flowered Petunia varieties, such as 'Suntory SP-R' (U.S. Plant Pat. No. 9,557), 'Sunberubu' (U.S. Plant Pat. No. 9,754), 'Sunbelochipi' (U.S. Plant Pat. No. 10,355), and 'Sunbelki' (U.S. Plant Pat. No. 11,558), having a semi-erect growth habit, short stems, a medium plant height, abundant branching, and a high resistance to heat, cold and rain. However, there are only a few Petunia varieties having a great profusion of flowers, a light yellowish pink with vivid reddish orange flower color, a very small flower size, and a high resistance to rain, heat, cold and diseases. Accordingly, this invention was aimed at obtaining a new variety having a light yellowish pink with vivid reddish orange flower color, and very small flowers combined with the above features.

The new variety of Petunia plant according to this invention originated from crossing of a Petunia plant variety named 'E2' (non-patented in the United States) and a Petunia plant variety named 'PE7' (non-patented in the United States).

Initially, 10 seedlings were selected in 1994 in view of yellowish pink petal coloration and were grown at Kitakoma-gun, Yamanashi-ken, Japan. From 1995 to 1996, open-pollination with those 10 seedlings was conducted at Youkaichi-shi, Shiga-ken, Japan. From that crossing, additional seedlings were obtained. In 1997 some seedlings were selected in view of the small flower size, light yellowish pink petals with vivid reddish orange coloration and semi-erect habit. These selected seedlings were grown in beds and pots on trial basis at Kitakoma-gun, Yamanashi-ken, Japan. In September 1998 one Petunia plant of the present inventions was selected. In 1999 the botanical characteristics were examined, using similar 'Sunbelki' variety and the 'Pearl Sky Blue' variety (non-patented in the United States) for comparison. As a result, it was concluded that this Petunia is distinguishable from any other variety, whose existence is known to me and is uniform and stable in its characteristics. This new variety of Petunia plant was named 'Sunbel-Apu'.

In the following description, the color-coding is in accordance with The R.H.S. Colour Chart of The Royal Horticultural Society, London, England. A color chart based on The Japan Color Standard for Horticultural Plants (J.H.S. Color Chart) has also been added for reference.

The main botanical characteristics of the 'E2' variety are as follows:

Plant:
- *Growth habit.*—Semi-erect.
- *Plant height.*—Medium, approximately 14 cm.
- *Spreading area of plant.*—Medium to large, approximately 18 cm.
- *Blooming period.*—May to September in the southern Kanto area, Japan.

Stem:
- *Thickness.*—Thin, approximately 2.1 mm.
- *Pubescence.*—Sparse.
- *Branching.*—Abundant with a superior branching propensity, and the secondary branches are particularly numerous.
- *Length of internode.*—Short, approximately 1.0 cm.

Leaf:
- *Shape.*—Lanceolate.
- *Length.*—Very short, approximately 2.4 cm.
- *Width.*—Very narrow, approximately 1.1 cm.
- *Color.*—Grayish olive green (R.H.S. No. 137B, J.H.S. No. 3716).
- *Thickness.*—Thin, approximately 0.3 mm.
- *Pubescence.*—Sparse to typical of the species.
- *Leaf attachment angle to stem.*—Slanted upward to horizontal.

Flower:
- *Facing direction.*—Slanted upward to horizontal.
- *Type.*—Single.
- *Shape.*—Funnel-shaped, with five petals.
- *Shape of petal tip.*—Round.
- *Waving of petal.*—Weak.
- *Lobation of petal.*—Shallow.
- *Diameter.*—Very small, approximately 2.7 cm.
- *Ground color of bi-colored petal.*—Pale orange yellow (R.H.S. No. 23D, J.H.S. No. 1903).
- *Color of center part.*—Vivid reddish orange (R.H.S. No. 34A, J.H.S. No. 0705).
- *Bottom color of the corolla throat.*—Brilliant yellow (R.H.S. No. 15B, J.H.S. No. 2204) .
- *Outside color of corolla tube.*—Brilliant yellow (R.H.S. No. 13C, J.H.S. No. 2505).
- *Reproductive organs.*—1 normal pistil and 5 normal stamens.
- *Fertility.*—Fertile, but self-incompatible.
- *Peduncle.*—Approximately 0.6 mm in thickness, and approximately 1.9 cm in length.
- *Physiological and ecological characteristics.*—High resistance to cold, rain, heat, drought and diseases, such as Powdery Mildew. The resistance to rain and heat is very strong.
- *Blooming.*—A bloom commonly lasts approximately 10 days on the plant. Pinching is not necessary to ensure continued blooming; however, it does tend to enhance bloom production somewhat.

The main botanical characteristics of the 'PE7' variety are as follows:

Plant:
- *Growth habit.*—Medium upright to spreading.
- *Plant height.*—Medium, approximately 14 cm.
- *Spreading area of plant.*—Medium, approximately 16 cm.
- *Blooming period.*—May to September in the southern Kanto area, Japan.

Stem:
- *Thickness.*—Thin, approximately 1.4 mm.
- *Pubescence.*—Sparse.
- *Branching.*—Abundant with a superior branching propensity, and the secondary branches are particularly numerous.
- *Length of internode.*—Short, approximately 1.2 cm.

Leaf:
- *Shape.*—Lanceolate.
- *Length.*—Very short, approximately 2.0 cm.
- *Width.*—Very narrow, approximately 0.7 cm.
- *Color.*—Grayish olive green (R.H.S. No. 137A, J.H.S. No. 3716).
- *Thickness.*—Thin, approximately 0.4 mm.
- *Pubescence.*—Sparse to typical of the species.
- *Leaf attachment angle to stem.*—Slanted upward to horizontal.

Flower:
- *Facing direction.*—Slanted upward.
- *Type.*—Single.
- *Shape.*—Funnel-shaped, with five petals.
- *Shape of petal tip.*—Round.
- *Waving of petal.*—Weak.
- *Lobation of petal.*—Shallow.
- *Diameter.*—Very small, approximately 2.4 cm.
- *Ground color of bi-colored petal.*—Strong yellowish pink (R.H.S. No. 38A, J.H.S. No. 0704).
- *Color of variegated pattern.*—Vivid red (R.H.S. No. 42A, J.H.S. No. 0707).
- *Bottom color of the corolla throat.*—Brilliant yellow (R.H.S. No. 15A, J.H.S. No. 2204).
- *Outside color of corolla tube.*—Vivid yellow (R.H.S. No. 13A, J.H.S. No. 2506).
- *Reproductive organs.*—1 normal pistil and 5 normal stamens.
- *Fertility.*—Fertile, but self-incompatible.
- *Peduncle.*—Approximately 0.7 mm in thickness, and approximately 1.2 cm in length.
- *Physiological and ecological characteristics.*—High resistance to cold, rain, heat, drought and diseases, such as Powdery Mildew.
- *Blooming.*—A bloom commonly lasts approximately 10 days on the plant. Pinching is not necessary to ensure continued blooming; however, it does tend to enhance bloom production somewhat.

The main botanical characteristics of 'Sunbelki' variety are as follows:

Plant:
- *Growth habit.*—Decumbent to medium upright.
- *Plant height.*—Approximately 18 cm.
- *Spreading area of plant.*—The stems commonly extend to a length of approximately 18 cm from the base.
- *Growth.*—Very vigorous with abundant branching, and a great profusion of blooms, with the entire plant remaining in bloom for a considerable period of time.

*Blooming period.*—April to late October in the southern Kanto area, Japan. The plant shape does not change throughout this period.

Stem:

*Thickness.*—Approximately 2.3 mm.

*Pubescence.*—Present.

*Branching.*—Abundant with a superior branching propensity, and the secondary branches are particularly numerous.

*Length of internode.*—Approximately 1.5 cm.

Leaf:

*Shape.*—Lanceolate.

*Length.*—Approximately 5.0 cm.

*Width.*—Approximately 1.4 cm.

*Color.*—Moderate olive green (R.H.S. No. 146B, J.H.S. No. 3508).

*Thickness.*—Very thin, approximately 0.2–0.4 mm.

*Pubescence.*—Sparse.

*Leaf attachment angle to stem.*—Slanted upward to horizontal.

Flower:

*Facing direction.*—Horizontal.

*Type.*—Single.

*Shape.*—Funnel-shaped, with five petals.

*Shape of petal tip.*—Mucronate.

*Waving of petal.*—Weak.

*Lobation of petal.*—Shallow.

*Diameter.*—Approximately 2.8 cm.

*Color of petals.*—Brilliant yellow (R.H.S. No. 12A, J.H.S. No. 2505). At low temperatures, it displays a dark reddish brown (R.H.S. No. 166A, J.H.S. No. 1310) main vein, and grayish reddish brown (R.H.S. No. 165A, J.H.S. No. 1317) secondary veins on the petals.

*Bottom color of the corolla throat.*—Strong brown (R.H.S. No. 166B, J.H.S. No. 1308) with a slight presence of dark reddish brown (R.H.S. No. 166A J.H.S. No. 1310) veins.

*Outside color of corolla tube.*—Light greenish yellow (R.H.S. No. 4C, J.H.S. No. 2904) with a slight presence of dark reddish brown (R.H.S. No. 166A, J.H.S. No. 1310) veins.

*Reproductive organs.*—1 normal pistil and 5 normal stamens.

*Fertility.*—Seeds are formed, but are infertile based on observations to date.

*Peduncle.*—Thin, approximately 0.7–0.8 mm in thickness, and approximately 1.9 cm in length.

*Physiological and ecological characteristics.*—High resistance to rain, heat, drought and diseases, such as Powdery Mildew. The resistance to rain and heat is very strong.

*Blooming.*—A bloom commonly lasts approximately 10 days on the plant. Pinching is not necessary to ensure continued blooming; however, it does tend to enhance bloom production somewhat.

The botanical characteristics for comparative purposes of the 'Pearl Sky Blue' variety are as follows:

Plant:

*Growth habit.*—Medium upright to spreading.

*Plant height.*—Medium, approximately 14 cm.

*Spreading area of plant.*—Medium to large, approximately 16 cm.

*Blooming period.*—May to September in the southern Kanto area, Japan.

Stem:

*Thickness.*—Thin, approximately 2.7 mm.

*Pubescence.*—Dense.

*Branching.*—Abundant.

*Length of internode.*—Short, approximately 1.3 cm.

Leaf:

*Shape.*—Elliptic.

*Length.*—Short, approximately 5.5 cm.

*Width.*—Narrow to medium, approximately 3.5 cm.

*Color.*—Strong yellow green (R.H.S. No. 144A, J.H.S. No. 3507).

*Thickness.*—Medium.

*Pubescence.*—Dense.

*Leaf attachment angle to stem.*—Horizontal to droopy.

Flower:

*Facing direction.*—Upward.

*Type.*—Single.

*Shape.*—Funnel-shaped, with five petals.

*Shape of petal tip.*—Round.

*Waving of petal.*—Weak.

*Lobation of petal.*—Shallow.

*Diameter.*—Small, approximately 5.5 cm.

*Color of petals.*—Strong purple (R.H.S. No. 83C, J.H.S. No. 8310).

*Bottom color of the corolla throat.*—Light greenish yellow (R.H.S. No. 3D, J.H.S. No. 2904).

*Outside color of corolla tube.*—Light greenish yellow (R.H.S. No. 3D, J.H.S. No. 2904).

*Reproductive organs.*—1 normal pistil and 5 normal stamens.

*Fertility.*—Fertile.

*Peduncle.*—Thin, and approximately 2.7 cm in length.

*Physiological and ecological characteristics.*—The resistance to cold, heat, disease and pests is moderate.

This new 'Sunbel-Apu' variety was asexually reproduced by the use of cuttings at Youkaichi-shi, Shiga-ken, Japan, and the homogeneity and stability thereof were confirmed. The characteristics of the new variety are reliably transmitted to subsequent generations by such asexual reproduction.

SUMMARY OF THE VARIETY

This new 'Sunbel-Apu' variety has a semi-erect growth habit with very small flowers having light yellowish pink color petals with a vivid reddish orange center. Thus, the new variety is very different from the similar 'Sunbelki' and the 'Pearl Sky Blue' varieties. The plant has a semi-erect growth habit, a compact plant shape, and abundant branching. The secondary branching is especially strong. The plant has a great profusion of blooms with the entire plant remaining in bloom for a considerable period of time. The blooming period commonly is late May to September. The flowers commonly remain open in the rainy season and the flowering duration is long. A whole plant remains in bloom for a considerable period of time.

BRIEF DESCRIPTION OF THE PHOTOGRAPH

FIG. 1 shows the flowers, foliage and overall growth habit of the new variety of Petunia plant.

DESCRIPTION OF THE NEW VARIETY

The botanical characteristics of the new and distinct 'Sunibel-Apu' variety are set forth hereafter. The plants were observed during November at Youkaichi-shi, Shiga-ken, Japan, and had been reproduced by the use of cuttings during September the year before.

Plant:

*Growth habit.*—Semi-erect.

*Plant height.*—Medium, approximately 15 cm.

*Spreading area of plant.*—The stems commonly extend to a length of approximately 14 cm from the base.

*Growth.*—Very vigorous with abundant branching and a great profusion of blooms with the entire plant remaining in bloom for a considerable period of time.

*Blooming period.*—May to September in the southern Kanto area, Japan. This can be compared to a number of other Petunia varieties that commonly begin blooming a number of weeks earlier.

Stem:

*Thickness.*—Thin, approximately 2.3 mm.

*Pubescence.*—Sparse.

*Branching.*—Abundant with a superior branching propensity. The secondary branches are particularly numerous.

*Length of internode.*—Short, approximately 1.4 cm.

Leaf:

*Shape.*—Lanceolate.

*Length.*—Very short, approximately 2.4 cm.

*Width.*—Very narrow, approximately 0.8 cm.

*Color.*—Moderate olive green (R.H.S. No. 138A, J.H.S. No. 3308).

*Thickness.*—Medium, approximately 0.6 mm.

*Pubescence.*—Sparse to medium.

*Leaf attachment angle to stem.*—Slanted upward to horizontal.

Flower:

*Facing direction.*—Upward to slanted upward.

*Type.*—Single.

*Shape.*—Funnel-shaped, with five petals.

*Shape of petal tip.*—Obtuse.

*Waving of petal.*—Weak.

*Lobation of petal.*—Shallow.

*Diameter.*—Very small, approximately 2.5 cm.

*Variegated pattern of corolla.*—At the center.

*Ground color of bi-colored petal.*—Light yellowish pink (R.H.S. No. 36A, J.H.S. No. 0702).

*Color of variegated pattern.*—Vivid reddish orange (R.H.S. No. 34A, J.H.S. No. 0705).

*Bottom color of the corolla throat.*—Vivid yellow (R.H.S. No. 15A, J.H.S. No. 2205).

*Outside color of corolla tube.*—Light yellow (R.H.S. No. 13C, J.H.S. No. 2203).

*Reproductive organs.*—1 normal pistil and 5 normal stamens.

*Fertility.*—Fertile, but self-incompatible.

*Peduncle.*—Approximately 0.7 mm in thickness, and approximately 1.2 cm in length.

*Physiological and ecological characteristics.*—High resistance to cold, rain, heat, drought and diseases, such as Powdery Mildew. The resistance to rain and heat is very strong.

*Blooming.*—A bloom commonly lasts approximately 10 days on the plant. Pinching is not necessary to ensure continued blooming; however, it does tend to enhance bloom production somewhat.

This new variety of Petunia plant is most suitable for flower bedding and potting, particularly in hanging pots and planters. It additionally is excellent for ground cover usage.

I claim:

1. A new and distinct variety of Petunia plant, substantially as herein illustrated and described, characterized particularly as to novelty by (A) a semi-erect growth habit, (B) forms an abundant number of flowers in a spike with a great profusion blooms and the entire plant remaining in bloom for a considerable period of time, (C) possesses a long flowering duration that commonly extends from late May to September, (D) forms flowers having a light yellowish pink petals with a vivid reddish orange center, and (E) a high resistance to rain, cold, heat, drought, diseases and pests.

* * * * *